(12) United States Patent
Lamichhane et al.

(10) Patent No.: US 12,150,753 B2
(45) Date of Patent: Nov. 26, 2024

(54) DEVICE, SYSTEM AND METHOD FOR PROVIDING A SKELETON MODEL

(71) Applicant: KONINKLIJKE PHILIPS N.V., Eindhoven (NL)

(72) Inventors: Bishal Lamichhane, Eindhoven (NL); Jens Muehlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 923 days.

(21) Appl. No.: 17/277,645

(22) PCT Filed: Sep. 19, 2019

(86) PCT No.: PCT/EP2019/075145
§ 371 (c)(1),
(2) Date: Mar. 18, 2021

(87) PCT Pub. No.: WO2020/058390
PCT Pub. Date: Mar. 26, 2020

(65) Prior Publication Data
US 2022/0022777 A1    Jan. 27, 2022

(30) Foreign Application Priority Data
Sep. 19, 2018  (EP) .................................... 18195442

(51) Int. Cl.
*A61B 5/11*   (2006.01)
*A61B 5/00*   (2006.01)
*G06T 17/00*  (2006.01)

(52) U.S. Cl.
CPC .......... *A61B 5/1114* (2013.01); *A61B 5/1128* (2013.01); *A61B 5/4561* (2013.01);
(Continued)

(58) Field of Classification Search
CPC ... G06T 17/00; G06T 2210/41; A61B 5/1114; A61B 5/1128; A61B 5/4561; A61B 5/684; A61B 5/7264; A61B 5/00; A61B 5/11
See application file for complete search history.

(56) References Cited

U.S. PATENT DOCUMENTS 9,892,611 B1 * 2/2018 Kusens ................... G06T 7/246
10,292,662 B2 * 5/2019 Kirenko .................... G06T 7/11
(Continued)

FOREIGN PATENT DOCUMENTS

CN    106959747 A    7/2017
JP    2014068714 A    4/2014
(Continued)

OTHER PUBLICATIONS

International Search Report and Written Opinion, International Application No. PCT/EP2019/075145, Mailed on Dec. 6, 2019.
(Continued)

*Primary Examiner* — Tuan H Nguyen

(57) ABSTRACT

The present invention relates to a device, system, method and computer program for providing a skeleton model, wherein the device comprises a joint identification unit configured to obtain an image and corresponding image data of the patient comprising depth information and to generate joint location data by localizing one or more joints of the patient in said image, a pose estimation unit configured to generate pose estimation data by estimating a pose of the patient using the joint location data and/or the image data, a sensor location unit configured to obtain body location data, comprising information about a location of a sensor on the patients body, and image location data, comprising information about the location of the sensor in the image, and to generate sensor location data, assigning a sensor location in the image to a body location of the patient, based on the
(Continued)

body location data and the image location data, an assignment unit configured to perform an assignment of the one or more joints to one or more body locations of the patient by using the joint location data, the pose estimation data and the sensor location data, and a skeleton modelling unit configured to generate a skeleton model of the patient based on the assignment of the joints to a body location.

14 Claims, 11 Drawing Sheets

(52) U.S. Cl.
CPC ............ *A61B 5/684* (2013.01); *A61B 5/7264* (2013.01); *G06T 17/00* (2013.01); *G06T 2210/41* (2013.01)

(56) References Cited

U.S. PATENT DOCUMENTS

2018/0047175 A1  2/2018  Wang et al.
2018/0049669 A1  2/2018  Vu et al.
2019/0299902 A1  10/2019  Nagasawa

FOREIGN PATENT DOCUMENTS

| | | |
|---|---|---|
| JP | 2015102913 A | 6/2015 |
| JP | 2016151966 A | 8/2016 |
| JP | 2017503225 A | 1/2017 |
| JP | 2017068424 A | 4/2017 |
| WO | 2012164482 A1 | 12/2012 |
| WO | 2015078735 A1 | 6/2015 |
| WO | 2018104359 A1 | 6/2018 |

OTHER PUBLICATIONS

Rocha, J. (n.d.). Skeltrack. Retrieved from Skeltrack: https://github.com/joaquimrocha/Skeltrack, Accessed Mar. 16, 2021.

Shotton, J. (2011). Real-time human pose recognition in parts from single depth images. CVPR, (pp. 1297-1304).

Ye, G. et al., "Performance Capture of Interacting Characters with Handheld Kinects", Computer Vision—ECCV 2012 pp. 828-841.

* cited by examiner

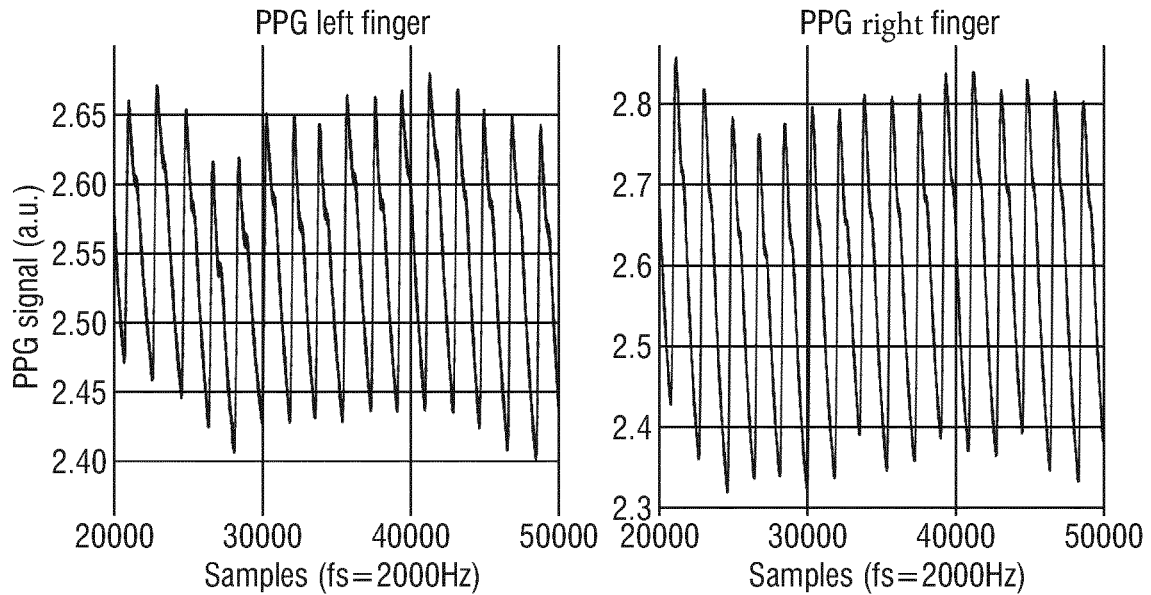
FIG.8A
FIG.8B
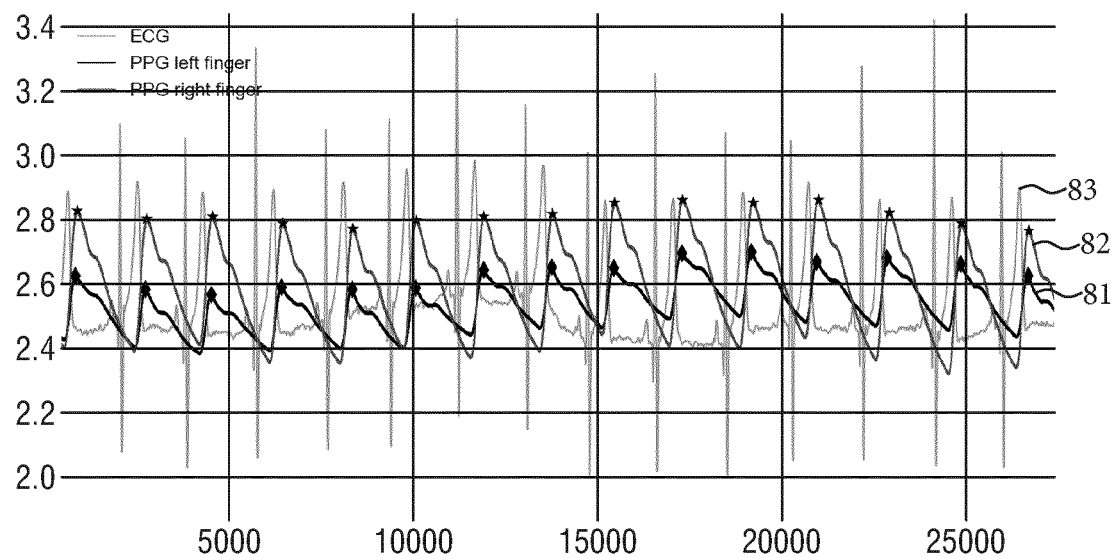
FIG.8C

DEVICE, SYSTEM AND METHOD FOR PROVIDING A SKELETON MODEL

This application is the U.S. National Phase application under 35 U.S.C. §371 of International Application No. PCT/EP2019/075145, filed on 19 Sep. 2019, which claims the benefit of European Application Serial No. 18195442.1, filed 19 Sep. 2018. These applications are hereby incorporated by reference herein.

FIELD OF THE INVENTION

The present invention relates to a device and system for providing a skeleton model and to a corresponding method and computer program for providing a skeleton model. The present invention further relates to a device for localizing a sensor on a patient's body.

BACKGROUND OF THE INVENTION

Automated methods for continuous patient activity monitoring improve clinical workflows and reduce the workload burden on clinical care providers. With automated monitoring, the concerned caregivers can be alarmed in time when some unusual patient behavior is detected. Further, continuous monitoring of the patient activity can be used for behavior profiling of the patient. Behavior profiles in turn can be linked to clinical conditions like mental disorders, agitation, depression, sleep disorders, etc. for diagnosis purposes.

A number of technologies have been investigated for automated patient monitoring. Camera based monitoring is one of the promising technologies for this purpose. With camera based monitoring positions, orientation and/or movement of visible body parts can be registered. Other monitoring methods work with wearable sensors like accelerometers. In contrast to cameras, however, said sensors only capture movement in a particular body part.

In general, fine movement information from different body parts is required to provide a reliable estimate of the activity being performed. For example, recognition of dangerous events like a patient trying to pull off a respiration mask would require movement information from both the hands and possibly also the head and the torso.

Skeleton models of the human body can be used to build applications for movement monitoring, activity recognition, and several other clinical and consumer applications. A skeleton model provides a succinct representation of the human body, representing all the major body parts and/or major joints in the body like the head, shoulders, elbows, hands, legs etc. In fact, a skeleton model of the body is a stick-figure like representation with the major joints in the body identified. Therefore, skeleton models allow for a reliable patient activity monitoring system.

A skeleton model of a body is generally obtained using depth imaging technology. Indeed, depth cameras (i.e. range imaging cameras or 3D cameras) are gaining popularity for skeleton model development because they do not suffer from limitations faced by 2D cameras like the sensitivity to dynamic illumination. A number of methods and solutions are available for skeleton model development from depth images. These methods are especially used for gaming applications. In such gaming applications, skeleton models are used to track the movement of body parts and/or joints for gaming control. More particularly, an identified joint location and corresponding body (part) movement is usually used to control a character in a game.

Though skeleton models using depth cameras have found an increasing use and popularity for gaming scenarios, so far, these solutions fail in clinical monitoring scenarios. This is due to the fact that subjects in hospital mostly lie in sleeping poses. Accordingly, application of skeleton models using depth imaging in a clinical monitoring scenario has not been thoroughly investigated. In a gaming scenario, the subject is directly facing the camera with all the major joints directly and distinctly visible. In contrast, within the clinical monitoring scenario, where the subject is mostly found in sleeping poses, the subject may not be directly facing the camera and the major joints may hence not be distinctly identifiable. In fact, the most challenging poses are those where the subject is lying on a side of his/her body.

Given a depth camera hung up to the ceiling above a patient bed—which, in fact, is the only feasible location for a camera—, the patient's body joints are distinctly visible when the patient is lying in a supine position. Therefore the skeleton model can be obtained reliably. In case the patient is lying on a side of his/her body, however, at least not all body joints are distinctly visible. In such a lateral position, especially for the upper body part, there are confusions between the joints in the left and right part of the body. In particular, the right and the left arms usually lie very close to each other in both the depth and spatial dimension.

Given such a complex posture, existing methods trying to provide skeleton models from depth imaging are not able to accurately distinguish right elbow and right hand from left elbow and left hand, for example. There is no reliable means to tell apart if a particular body-part region is a left elbow or a right elbow, since these regions are very close to each other in particular poses. The same confusion holds also for the left and the right hand. Even existing deep learning based algorithms suffer from confusion in accurately identifying which joints belong to left body parts and which joints belong to right body parts. This leads to skeleton models with the right shoulder being linked with the left elbow and hand and left shoulder being linked with right elbow and hand.

Another factor limiting the accuracy of posture detection with depth cameras is that the head orientation is not a reliable indicator of the posture of the body corpus.

Accordingly, the reliability of a skeleton model may be highly compromised and reliable patient monitoring cannot be guaranteed. While for gaming applications a gamer may sometimes also be found in a position where it is hard to tell apart respective body regions, a failure in the correct assignment of body regions may not be life-threatening. However, in patient monitoring the monitoring results have to be absolutely reliable.

WO 2015/078735 A1 discloses a device and method for obtaining pulse transit time and/or pulse wave velocity information of a subject. Based on a set of image frames of a subject and detected motion of body parts of the subject regions of interest are selected from different non-moving body parts and pulse transit time and/or pulse wave velocity information is obtained from acquired PPG signals extracted from different regions of interest and the respective determined physical distance between the respective regions of interest.

WO 2018/104359 A1 relates to the determination of pulse wave velocity, for example for blood pressure monitoring, and in particular during sleep.

U.S. Pat. No. 9,892,611 B1 discloses a method and system that allows healthcare providers, hospitals, skilled nursing facilities and other persons to monitor disabled, elderly or other high-risk individuals to prevent or reduce falls and/or mitigate the impact of a fall by delivering automated notification of "at risk" behavior and falls by such an individual being monitored where assistance is required. Two systems are used to identify patients, a skeletal tracking system, which identifies patients by biometric indicators, and a virtual blob detection system.

SUMMARY OF THE INVENTION

It is an object of the present invention to provide a solution allowing for reliable and accurate skeleton model building. A particular object of the present invention is to avoid ambiguities with respect to body-part recognition in clinical patient monitoring.

In a first aspect of the present invention a device for providing a skeleton model of a patient is presented, the device comprising:

a joint identification unit configured to obtain an image and corresponding image data of the patient comprising depth information and to generate joint location data by localizing one or more joints of the patient in said image, a pose estimation unit configured to generate pose estimation data by estimating a pose of the patient using the joint location data and/or the image data, a sensor location unit configured to obtain body location data, comprising information about a location of a sensor on the patient's body, and image location data, comprising information about the location of the sensor in the image, and to generate sensor location data, assigning a sensor location in the image to a body location of the patient, based on the body location data and the image location data, an assignment unit configured to perform an assignment of the one or more joints to one or more body locations of the patient by using the joint location data, the pose estimation data and the sensor location data, and a skeleton modelling unit configured to generate a skeleton model of the patient based on the assignment of the joints to a body location.

In a second aspect of the present invention a system for providing a skeleton model of a patient is presented, the system comprising:

a device for providing a skeleton model of a patient in accordance with at least one embodiment as disclosed herein, and one or more sensors configured to generate one or more sensor signals by detecting one or more vital signs of the patient and/or a depth camera configured to acquire an image of the patient and to generate corresponding image data comprising depth information.

In a third aspect of the present invention a method for providing a skeleton model of a patient is presented, the method comprising the steps of:

obtaining an image and corresponding image data of the patient comprising depth information and generating joint location data by localizing one or more joints of the patient in said image, generating pose estimation data by estimating a pose of the patient using the joint location data and/or the image data, obtaining body location data, comprising information about a location of a sensor on the patient's body, and image location data, comprising information about the location of the sensor in the image, and generating sensor location data assigning a sensor location in the image to a body location of the patient based on the body location data and the image location data, performing an assignment of the one or more joints to one or more body locations of the patient by using the joint location data, the pose estimation data and the sensor location data, and generating a skeleton model of the patient based on the assignment of the joints to a body location.

In further aspects of the present invention, there is provided a corresponding computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed system, method and computer program and medium have similar and/or identical preferred embodiments as the claimed device, in particular as defined in the dependent claims and as disclosed herein.

The present invention is based on the idea to provide a device that allows for improved skeleton model development. Above all, the reliability and accuracy of skeleton models is intended to be increased, in particular in a clinical setting with patients possibly lying on their side in bed, possibly even huddled together. In such complex settings the device shall particularly be capable to tell apart body parts, in particular joints, with respect to their respective side of the body. More particularly, a device shall be provided which is able to accurately assess the location of the upper left and upper right body parts. This in turn allows for a more reliable and accurate skeleton model development.

First, an initial estimation of the location of the patient's joints is made using a depth image and corresponding depth image data, i.e. image data comprising depth information. Preferably, at least the patient's major joints are located in the image, wherein the term "joints" is to be interpreted in a broad manner and particularly comprises any one of the head, shoulders, elbows, wrists, butt (in particular the butt bone), knees and heels. To infer the location of joints, the joints of the patient first have to be identified, i.e. particular image regions have to be identified to represent joints. This may be achieved by common image recognition programs. In fact, a number of methods have been proposed for joint location identification. While some programs use heuristic rules for joint location identification, there also exist advanced data-driven approaches. For example, a random forest classifier may be trained to identify a body patch, i.e. an image region of a particular size, as corresponding to a particular joint type.

However, even though joint identification (implying identifying if there is a joint in an image) and location may be accompanied by identifying a joint with respect to its type or location within the patient's body, a reliable disambiguation between joints corresponding to left and right body parts, for example, cannot be performed by this unit. In fact, said unit primarily seeks to find out which image parts represent joints, possibly with a predetermined probability.

Knowing the joint locations of the patient in the image, the pose estimation unit may estimate the patient's position and orientation in his/her bed. Apart from the joint location data provided by the joint location unit the pose estimation unit may likewise use the image data corresponding to the depth image showing the patient and infer the pose information from said data.

Generally pose estimation can be performed using common image recognition algorithms, for example by training a machine learning model, in particular a deep learning model.

On the other hand, the joint locations may be used to infer the patient's pose. However, in order to get a reliable pose estimation preferably at least 5 joints (head, 2 shoulder and 2 elbow/hand joints) have to be located and provided by the joint identification unit.

In the assignment unit an assignment between the locations of the one or more joints in the image to one or more body locations of the patient is performed.

To this end the patient's position and orientation in the image, i.e. his posture/pose, and the joint location data localizing the joints in his body are used. Apart from that, the assignment unit obtains sensor location data.

The sensor location data are data assigning a location of a patient sensor to a body location of the patient and to a location in the image. For example, the sensor location data may provide information that there is attached a photoplethysmography, PPG, sensor on the patient's right hand. Furthermore, the sensor location data provides information at which coordinates of the image said sensor is located.

It is to be understood, that the meaning of terms like "left", "right", "upper" or "lower" with respect to body locations is pre-determined for the assignment unit and possibly other units of the device.

The sensor location data are generated in the sensor location unit by combining body location data and image location data, i.e. data comprising information about the location of the sensor on the patient's body and comprising information about the location of the sensor in the image. In particular, body location data may be obtained from a patient monitor, for example.

Once the sensor location both with respect to the patient's body and the image is known and the posture of the patient in his bed is known, the assignment unit assigns the location of the one or more joints to one or more body locations of the patient.

To be more precise, apart from data describing the patient's pose, the assignment unit is configured to receive information about a sensor location. Said sensor location data then support the assignment of joints to respective body regions. Apart from the given data, any prior information about the probability of a joint belonging either to the left and right side of the body, may also be used in this processing stage. In other words, in the proposed device, secondary information sources are used to support a disambiguation of body parts. This is especially helpful for patients lying in a sleeping pose on one side of their body, since there are difficulties to accurately identify the joints in the left and right side of the upper body.

For example, in a first step the assignment unit may assign the joints identified to one or more body regions using the joint location data and the pose estimation data. From the joint identification data the position of joints in the image is known and from the pose estimation data the position/posture of the patient in the image is known. Due to their location within the image the joints can be assigned to respective body parts.

However, said first assignment may not be correct due to the aforementioned difficulties for particular body postures. In particular, the body side of joints of the upper body part may be confused in this assignment. Therefore, in a second step the sensor location data are used to support and possibly correct the first assignment. For example, the sensor location data may comprise information that a PPG sensor is located at the patient's right forefinger and that a blood pressure, BP, sensor is attached to the patient's left upper arm. At the same time the sensor location data provide information about the location of the respective sensors within the image, for example in the form of image coordinates. Accordingly, the positions of the patient's right forefinger and the patient's left upper arm in the image are known. Hence, joints identified to be at a sensor position, i.e. located in a predetermined distance from the sensor position, can then be unambiguously allocated to a respective body region. For example, a joint identified to be at the location of the PPG sensor can be assigned unambiguously to the patient's right forefinger. Accordingly, it can be excluded that said joint belongs to the patient's left finger.

In general, the more joints are located and the more sensor positions (both with respect to the image and their location on a patient's body) are known, the higher may be the quality of the joint assignment. In particular, the available joint locations may be unambiguously assigned to either belonging to the left side of the patient's body or the right side of the body.

A precise assignment of body joints with regard to the patient's posture then allows for modelling a correct skeleton model of the patient. To generate a skeleton model the joints are linked according to the body regions they (are inferred to) belong to by straight lines. Accordingly, the skeleton modelling unit generates a stick-figure like representation with the major joints in the body identified. In fact, the skeleton modelling unit may generate the skeleton model using a best-fit algorithm.

In an embodiment, the device for providing a skeleton model of a patient further comprises a sensor information unit configured to obtain a sensor signal corresponding to a vital sign of the patient and to generate the body location data and/or pose estimation data based on said sensor signal.

Preferably, the sensor signal contains information about a vital sign of the patient as measured by at least two sensors, wherein at least one sensor is attached to the patient on his/her left body part and at least one other sensor is attached to the patient on his/her right body part. Furthermore, the position of the respective sensor is approximately at the same height of the patient's body. Given said setting, the physiological differences between left and right side of the body lead to different sensor readings of sensors corresponding to left and right side of the body. However, measurements from a single sensor and comparison with relevant reference values are also conceivable for generating body location data and/or pose estimation data. For example, ECG data may be used for the estimation of the patient's body posture. In fact, the orientation of the heart axis depends on the body's position and orientation in the earth's gravitational field. Therefore, different body postures result in reliable and reproducible ECG signal changes due to different projections of the heart electrical pattern vs. the body surface. Accordingly, by comparison with relevant reference signals ECG data provide information about the patient's posture in his/her bed.

The sensor signal may be obtained directly from a sensor, wherein said sensor may either be attached to the patient's body or the sensor monitors the patient's vital signs from a distance with a camera, for example. However, the sensor signal may also be obtained from an intermediate device.

In another embodiment, the device further comprises a sensor recognition unit configured to generate image location data by localizing the sensor in the image.

This may be achieved by using a particular marker attached to the sensor, for example, wherein said marker may comprise a striking color, pattern, shape or reflectivity. For example, a finger PPG sensor may be identified and localized by a square pattern on the side of the sensor turned away from the skin and a wire connected to the sensor.

In another embodiment, the pose estimation unit is configured to generate the pose estimation data further using the sensor location data.

For example, information that a BP sensor is attached to a patient's upper right arm may help distinguish the upper right arm from other body parts and hence may help figuring out the patient's pose.

In a preferred embodiment, the sensor signal corresponding to a vital sign comprises any one of electrocardiography data, photoplethysmography data, blood pressure data, body temperature data, blood oxygen saturation data, pulse rate data, pulse strength data and pulse arrival time data.

Electrocardiography, ECG, data comprise any one of P-wave data, data corresponding to the QRS complex, in particular data of the R-peak, and T-wave data, for example.

Photoplethysmography, PPG, is an optical technique used to detect volumetric changes in blood in peripheral circulation. PPG data particularly comprise data about a pulsatile ("AC") physiological waveform attributed to cardiac synchronous changes in the blood volume with each heart beat and a superimposed waveform on a slowly varying ("DC") baseline with various lower frequency components attributed to respiration. A PPG signal is usually obtained by a pulse oximeter.

As an example, the sensor information unit may be configured to obtain two PPG signals and an ECG signal, wherein the two PPG signals correspond to measurements made on a left and on a right finger of the patient, respectively. From particular features of the different signals information about the respective sensor locations, in particular information whether the PPG sensors are attached to a left or a right finger may be deduced. One such feature is the pulse arrival time, PAT, which is the duration it takes for the pulse to arrive at a particular body location. PAT may be calculated as the time delay between an R-peak in the ECG a corresponding maximum value of PPG waveform. PAT may be measured for both the left and the right body side of the patient. As there exists a minor difference in the path lengths from the heart to the left and right finger sites, there also exists a difference in the respective pulse arrival times. Due to the position of the heart in the human body, the PAT corresponding to the left finger of the patient is usually shorter than the PAT corresponding to the right finger. Hence, the PPG sensors can be easily distinguished by the sensor information unit to generate sensor location data assigning the locations of the PPG sensors to the left and right finger, respectively. When only a single PPG sensor is used, the PPG signal obtained from the sensor can still be assigned to have originated from the left or the right side of the body using previously obtained reference values (either derived from the patient or from a population cohort similar to the patient).

Aside from the pulse arrival time, several other PPG based features could be used by the sensor information unit to differentiate and deduce if the recorded signal is coming from the left side or the right side of the body. Said other PPG based features may comprise stiffness index and/or second-derivatives based PPG morphological features. Accordingly, there may be provided a classifier in the sensor information unit which is trained to use one or more PPG features to differentiate if a signal has been acquired from the left or the right side of the body.

In an advantageous embodiment, the pose estimation unit is configured to distinguish between a supine pose, wherein the patient is lying in a supine pose, a prone pose, wherein the patient is lying prone, and a side pose, wherein the patient is lying on a side of his or her body.

However, the pose estimation unit may also be configured to further identify an abdominal pose and/or poses (i.e. postures) that may not be clearly allocated to the beforementioned poses, such as a rolled up pose. With appropriate training examples, such poses can be detected with a trained machine learning model using the depth image as input.

In a further embodiment of the device for providing a skeleton model, the pose estimation unit is configured to estimate the pose of the patient by identifying a distribution of the one or more joints in the image.

In supine or abdominal positon, the joints are symmetrically distributed about an axis ranging from the patient's head to his/her buttocks. When lying on a side, however, the joints are clustered towards one side of said body axis. Hence, in case that significantly more joints are found right of the body axis then left from the body axis (as viewed from a camera above the patient), the pose identification unit assumes that the patient is lying on his left side with his arms and legs tilted to the right side of the bed.

In yet another embodiment of the device, the joint identification unit is configured to localize one or more extreme points in the image, wherein the pose estimation unit is configured to estimate the pose of the patient by identifying a distribution of said extreme points in the image.

Similar to the position of joints, when lying in a supine position, the extreme points in a depth image are symmetrically distributed around the major body axis (i.e. sagittal axis). When lying on a side of the body, however, the points are clustered to one side of the major body axis.

In some methods, a joint location is identified based on extreme points in the image, wherein extreme points are identified by contrast differences and/or body curvatures with respect to their surrounding areas, for example. Further, the features of paths from the body centroid, as estimated by such a common method, to identified extreme points is then used to classify said extreme points as a particular joint type.

In an advantageous embodiment, the joint identification unit (identifies and) localizes the one or more joints using a machine learning method, particularly a deep learning algorithm, more particularly a convolutional neural network.

Convolutional Neural Network (CNN) based architecture may be trained using depth image patches from various body parts. The trained network may then be able to take an image segment and identify it as being one of a joint type or not.

In a further embodiment, the device for providing a skeleton model of a patient further comprises a tracking unit configured to track movements of the patient based on two or more subsequent depth images and the corresponding two or more skeleton models.

In particular, the positions of extreme points and/or identified joints is compared. There may also take place a comparison with respect to the estimation of the patient's pose. From the differences detected a direction of a movement of one or more body part may be inferred. Accordingly, the patient's movements may be tracked, particularly if more than two images are compared with each other over a longer amount of time. In some advanced methods, there may be used a tracking engine to smooth the changes in the skeleton models from frame to frame.

In yet a further embodiment of the device, the tracking unit is configured to perform a comparison between the two or more skeleton models, wherein the joint location unit is configured to adapt the joint location data based on said comparison and/or wherein the skeleton modelling unit is configured to adapt the skeleton models based on said comparison. There likewise may be adapted the estimation of the patient's pose or the analysis with respect the extreme points. In fact, there solely may be an adaption of the inferred joint locations and/or extreme point locations etc., however, there may also take place an adaption of the methods used in the joint identification unit and/or pose estimation unit.

There is further presented a device for localizing a sensor on a patient's body, the device comprising a comparison unit configured to obtain a left sensor signal and a right sensor signal corresponding to a vital sign of the patient, wherein the left sensor signal is obtained from a left sensor detecting the vital sign on a left part of the patient's body and the right senor signal is obtained from a right sensor detecting the vital sign on a right part of the patient's body, and to perform a comparison of a feature of the left and right sensor signals with each other and/or with a reference value, an analysis unit configured to generate body location data by localizing the left sensor and the right sensor on the patient's body based on the comparison.

BRIEF DESCRIPTION OF THE DRAWINGS

These and other aspects of the invention will be apparent from and elucidated with reference to the embodiment(s) described hereinafter. In the following drawings:

FIGS. 8A and 8B show PPG signals simultaneously obtained from a patient's left and right finger, FIG. 8C shows the same PPG signals along with a simultaneously measured ECG signal.

DETAILED DESCRIPTION OF THE EMBODIMENTS

Figure 1:
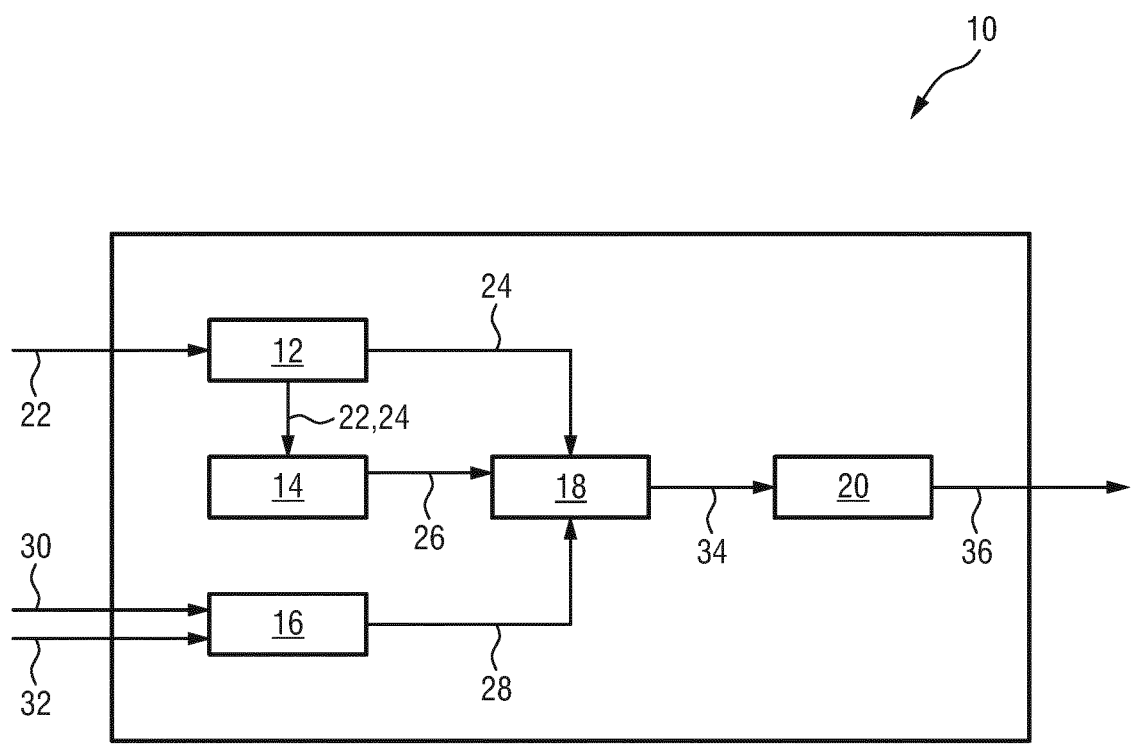
FIG. 1 shows a schematic diagram of a first embodiment of the device for providing a skeleton model of a patient according to the present invention.

FIG. 1 shows a schematic diagram of a first embodiment of the device 10 for providing a skeleton model of a patient according to the present invention. The device 10 comprises a joint identification unit 12, a pose estimation unit 14, a sensor location unit 16, an assignment unit 18 and a skeleton modelling unit 20.

In this embodiment, the joint identification unit 12 is configured to obtain an image of a patient and corresponding image data 22, wherein said image data 22 comprises depth information. Using the image data 22, the joint identification unit 12 is configured to identify and localize one or more joints of the patient in said image data 22. In other words, the joint identification unit 12 is configured to assign joints to locations in the image represented by the image data 22. The generated joint location data 24 assigning joints identified to locations in the image is then provided to both the pose estimation unit 14 and the assignment unit 18. The pose estimation unit 14 is further provided with the image data 22 from the joint identification unit 12.

Using the image data 22 and the joint location data 24, the pose estimation unit 14 generates pose estimation data 26 by estimating a pose of the patient. In this embodiment, pose estimation is performed using standard image recognition algorithms and matching with the joint location data 24. The pose estimation data 26 is then provided to the assignment unit 18.

Simultaneous to the reception of image data 22 by the joint identification unit 12, the assignment unit 18 obtains sensor location data 28, wherein said sensor location data 28 assign a sensor location in the image to a body location of the patient. The sensor location data 28 are generated by the sensor location unit 16 by linking body location data 30 to image location data 32, wherein the body location data 30 comprises information about the location of a sensor on the patient's body and wherein the image location data 32 comprises information about the location of the sensor in the image represented by the image data 22.

Once the joint location data 24, the pose estimation data 26 and the sensor location data 28 are provided to the assignment unit 18, said unit is configured to perform an assignment 34 of the one or more joints of the patient as identified and located by the joint identification unit 12 to one or more body locations of the patient. In order to do so, there is performed a first assignment using only the joint location data 24 and the pose estimation data 26. In a second step, the assignment of the first step is corrected using the sensor location data 28. The corrected assignment 34, i.e. the assignment without ambiguities concerning body locations of the joints, is then provided to the skeleton modelling unit 20.

The skeleton modelling unit 20 then generates a skeleton model 36 from said ambiguity-free assignment 34. In particular, the skeleton modelling unit 20 is configured to generate a stick figure by connecting the unambiguously identified joints by straight lines.

Figure 2:
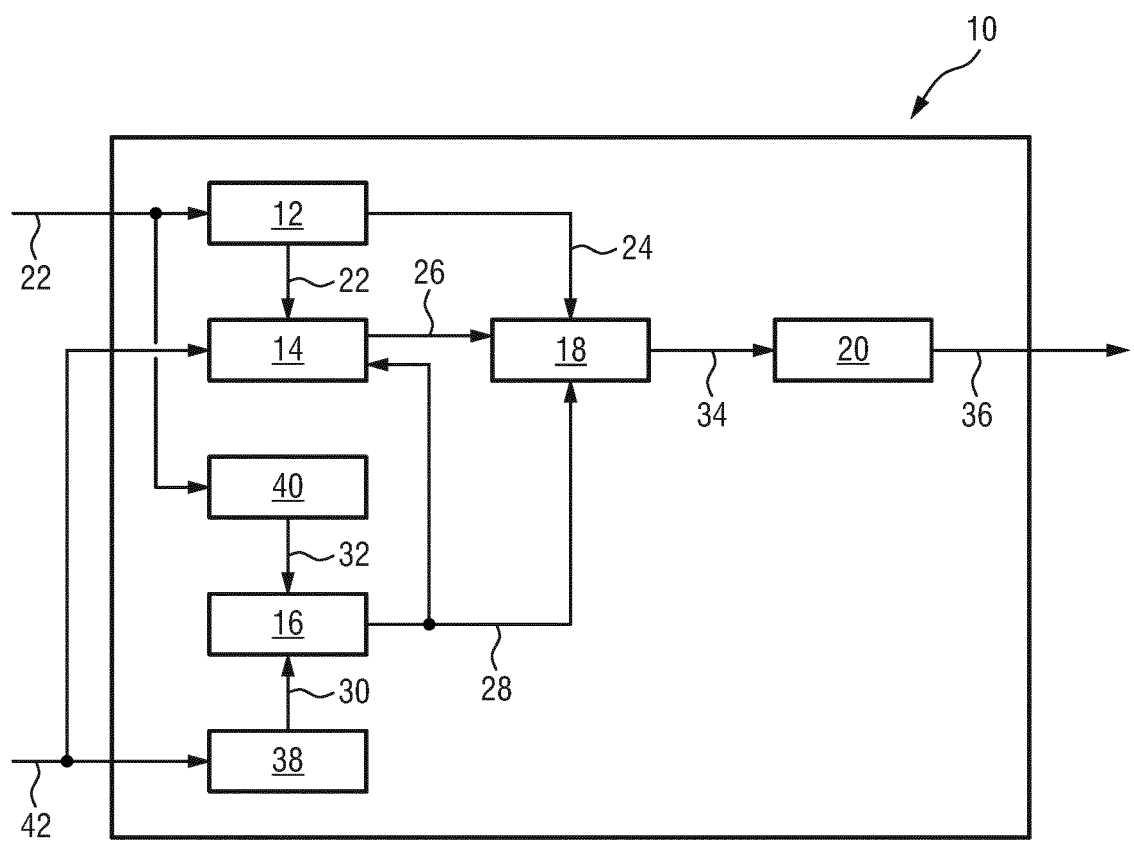
FIG. 2 shows a schematic diagram of a second embodiment of the device for providing a skeleton model of a patient according to the present invention.

FIG. 2 shows a schematic diagram of a second embodiment of the device 10. In this embodiment the device 10 comprises a joint identification unit 12, a pose estimation unit 14, a sensor location unit 16, an assignment unit 18, a skeleton modelling unit 20, a sensor information unit 38 and a sensor recognition unit 40.

Like in the first embodiment of the device 10 the joint identification unit 12 in this embodiment is configured to localize one or more joints of the patient in a depth image represented by image data 22. However, the corresponding joint location data 24 are only provided to the assignment unit 18. In particular, the joint location data 24 are not provided to the pose estimation unit 14. In fact, the image and the corresponding image data 22 are just forwarded to the pose estimation unit 14. However, pose estimation in this embodiment is further supported by sensor signals 42 and sensor location data 28.

The sensor location data 28 are provided by the sensor location unit 16 and comprises information about a position of sensors attached to the patient both with respect to the patient's body and with respect to the image. In order to generate the sensor location data 28 the sensor location unit 16 is provided with input from the sensor information unit 38 and the sensor recognition unit 40.

Given, for example, that the patient has a PPG sensor on both a left and a right finger and an ECG sensor on his chest, the sensor recognition unit 40 is configured to identify and localize these sensors within the image. In order to (identify and) localize the sensors in the image particular recognition algorithms may be used. By localizing the sensors in the image, image location data 32 are generated. At the same time, the sensor signals 42 of said sensors are analyzed in the sensor information unit 38. In particular, the sensor signals 42 are used to find the body location they originate from. To this end, the sensor information unit 38 may derive the pulse arrival time from the PPG signals and compare the respective times with reference values corresponding to particular body parts. Once both information about the location of the sensors with respect to patient body and image is known, the sensor location unit 16 links the information to generate sensor location data 28 assigning a sensor location in the image to a body location of the patient.

Using the sensor location data 28 pose estimation in the pose estimation unit 14 may be supported. With the sensor signals 42 themselves, in particular with the ECG data, the pose estimation may be refined further. This is due to the fact that ECG data are subject to changes when the patient moves in the earth's gravitation of field. To this end, reference values of ECG data stored in the pose estimation unit 14 may be provided and the measured ECG signals may be compared to the reference values to find out about the patient's posture in his bed. In particular, the ECG data may help to distinguish between a supine and an abdominal position of the patient. In fact, the ECG signal can be used to distinguish between various distinct body poses.

The estimated pose of the patient is then provided to the assignment unit 18 in the form of pose estimation data 26 for further processing.

Figure 3:
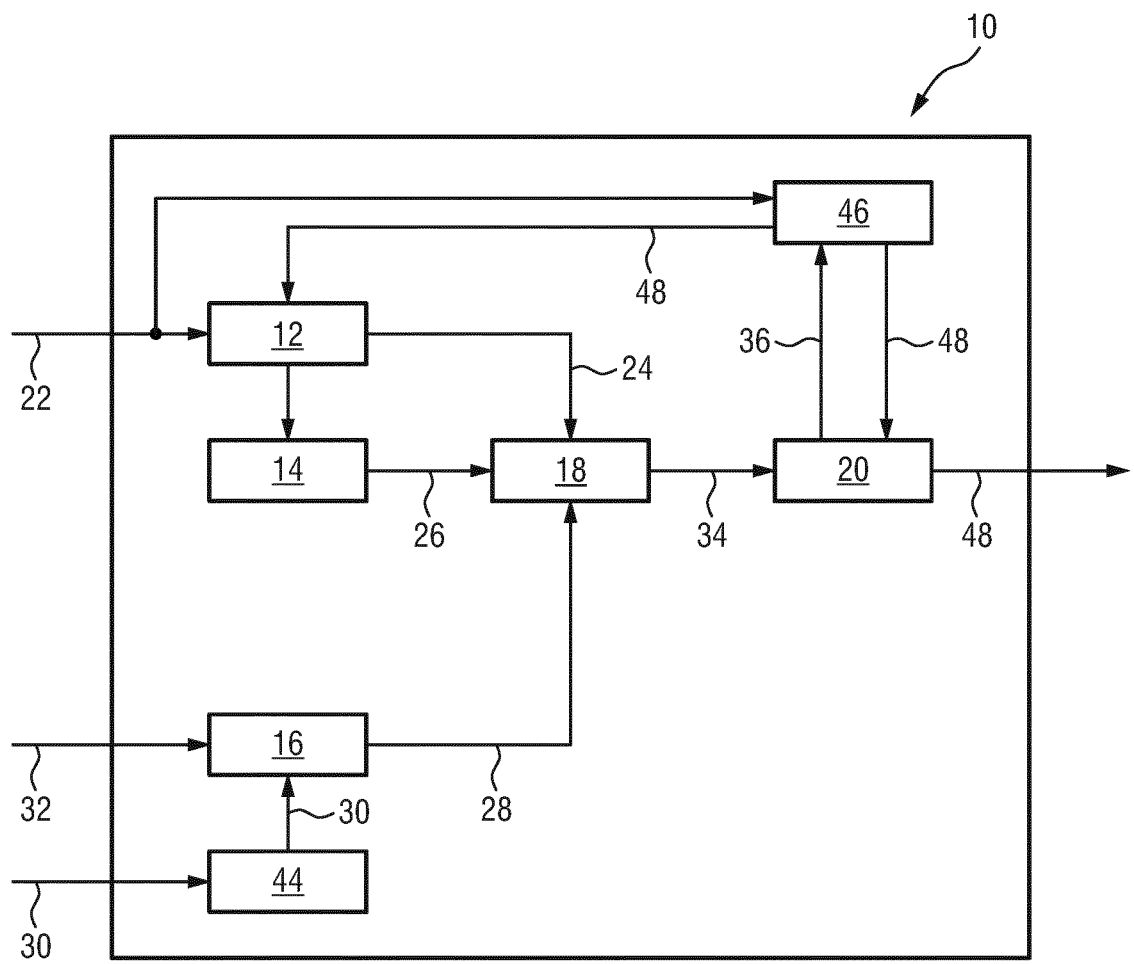
FIG. 3 shows a schematic diagram of a third embodiment of the device for providing a skeleton model of a patient according to the present invention.

FIG. 3 shows a schematic diagram of a third embodiment of the device 10 for providing a skeleton model of a patient according to the present invention. In this embodiment, the device 10 comprises a joint identification unit 12, a pose estimation unit 14, a sensor location unit 16, an assignment unit 18, a skeleton modelling unit 20, a user interface 44 and a tracking unit 46.

The joint identification unit 12 is configured to obtain two or more images and corresponding image data 22 of the patient. Joint location, pose estimation and joint assignment 34 are performed for each image.

To improve the joint assignment 34 the assignment unit 18is provided with sensor location data 28 defining both the position of a sensor within the images 22 and on the patient. The sensor location data 28 are generated in the sensor location unit 16 using sensor information data 30 and sensor recognition data 32. In this embodiment, the sensor information data 32, i.e. data comprising information about sensor positions with respect to the patient, is obtained from a user interface 44. In particular, users, i.e. clinical staff, for example, may enter information corresponding to the sensor location manually in the user interface.

After the joint assignment 34, there is generated a skeleton model 36 for each image. The skeleton models 36 of subsequent images 22 are then provided to the tracking unit 46. Furthermore, the tracking unit 46 is configured to obtain the original image data 22 corresponding to the skeleton models 36.

The tracking unit 46 particularly compares subsequent images represented by image data 22 with each other and also skeleton models 36 corresponding to subsequent images. Based on the comparison results, the tracking unit 46 corrects and/or refines the skeleton model 36 of each image and hence generates corrected skeleton models 48. However, the tracking unit 46 may also sort out certain skeleton models 36. For example, if two subsequent patient images 22 do not differ substantially, the corresponding skeleton models 36 should neither differ substantially. However, in case that the skeleton models 36 of both images 22 differ, then the tracking unit 46 assumes that at least one of said models 36 is wrong. By comparison with further images 22 and skeleton models 36 deficient skeleton model(s) can be identified and either be corrected or get sorted out. Corrected skeleton models 48 are then returned to the skeleton modelling unit 20 and may be used for further processing.

Moreover, the tracking unit 46 in this embodiment is configured to provide the corrected skeleton model(s) 48 to the joint identification unit 12. In the joint identification unit 12 said model(s) 48 may be used to localize joints in a subsequent patient image represented by image data 22.

There are also embodiments conceivable, where the corrected skeleton models 48 or other skeleton models may be used to support pose estimation and/or assignment 34 of joints to body locations.

Figure 4:
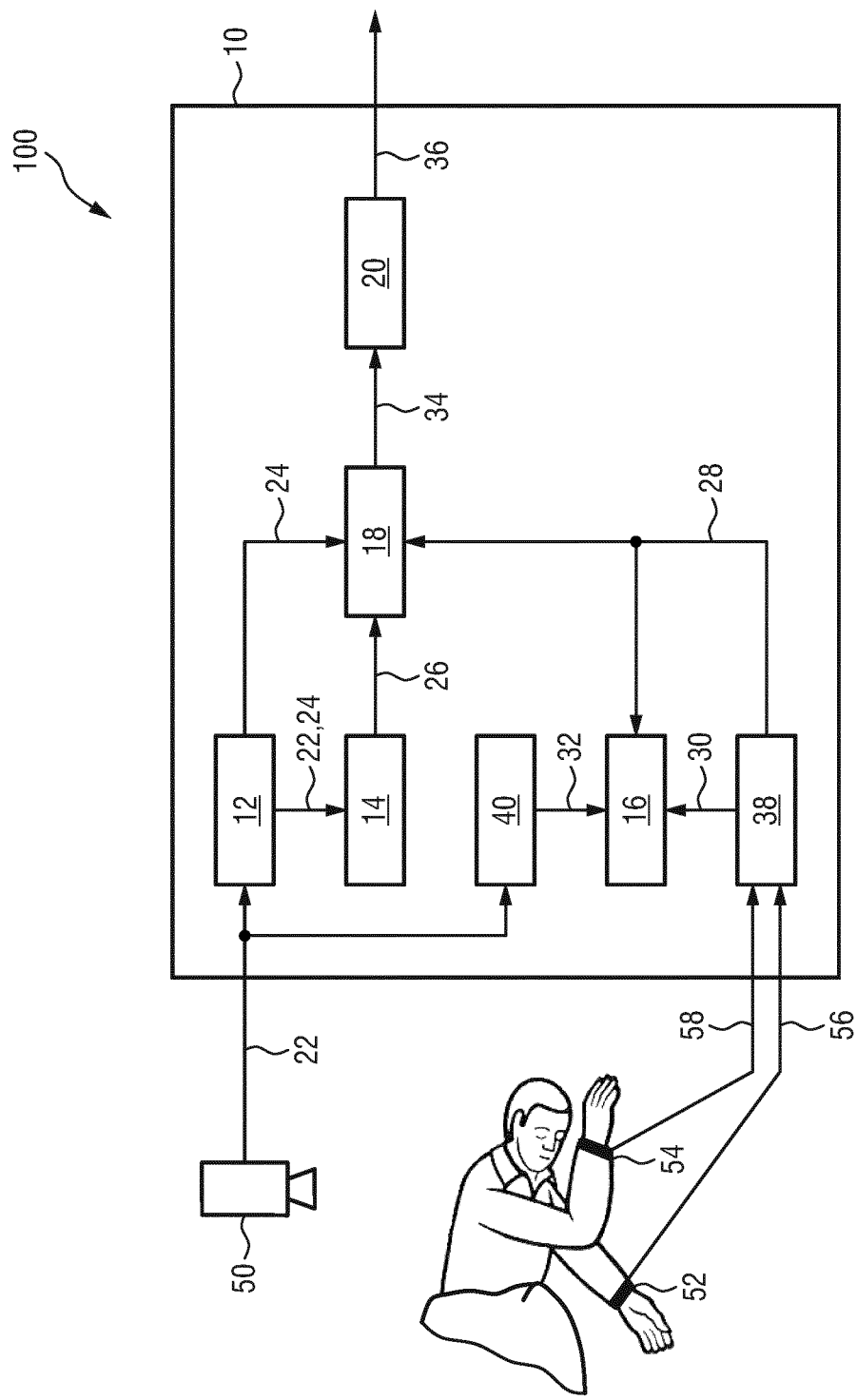
FIG. 4 shows a schematic diagram of a first embodiment of a system for providing a skeleton model of a patient according to the present invention.

FIG. 4 shows a schematic diagram of a first embodiment of a system 100 for providing a skeleton model of a patient according to the present invention. The system 100 comprises a device 10, a camera 50 and a left PPG sensor 52 attached to the patient's left wrist and a right PPG sensor 54 attached to the patient's right wrist. The device 10 comprises a joint identification unit 12, a pose estimation unit 14, a sensor location unit 16, an assignment unit 18, a skeleton modelling unit 20, a sensor information unit 38 and a sensor recognition unit 40.

The left and right PPG sensors 52 and 54 provide left and right PPG signals 56 and 58, respectively. The sensor information unit 38 analyzes the PPG signals 56 and 58 to find the patient's pulse strength at each wrist. Due to the location of the human heart pulse strength at the left wrist is generally higher than at the right wrist. This applies to other equivalent left and right body regions as well. By comparing the pulse strengths provided by the PPG signals 56 and 58 the sensor information unit 38 is capable to figure out from which of the sensors the PPG signals 56 and 58 originate. In case there cannot be found any pulse strength difference, for example because the sensor signals 56 and 58 are too weak, the sensor information unit 38 generates body location data 30 based on default clinical practices concerning the side of the body (left or right hand) the sensors 52 and 54 are attached to.

The body location data 30 found by the unit 38 is then provided to the sensor location unit 16, which further obtains sensor recognition data 32 comprising information about the location of the PPG sensors 53 and 54 in the image represented by image data 22. The sensor recognition data 32 and the body location data 30 are then joined together in the form of sensor location data 28.

The sensor location data 28 are subsequently provided to the assignment unit 18 of the device 10. The assignment unit 18 then evaluates the joint location data 24, the pose estimation data 26 and the sensor location data 28 to find out the correct patient's posture with the joints being correctly assigned to their corresponding body regions. Subsequently, the skeleton modelling unit 20 creates a skeleton model 36 based on the assignment 34 of the assignment unit 18.

Figure 5:
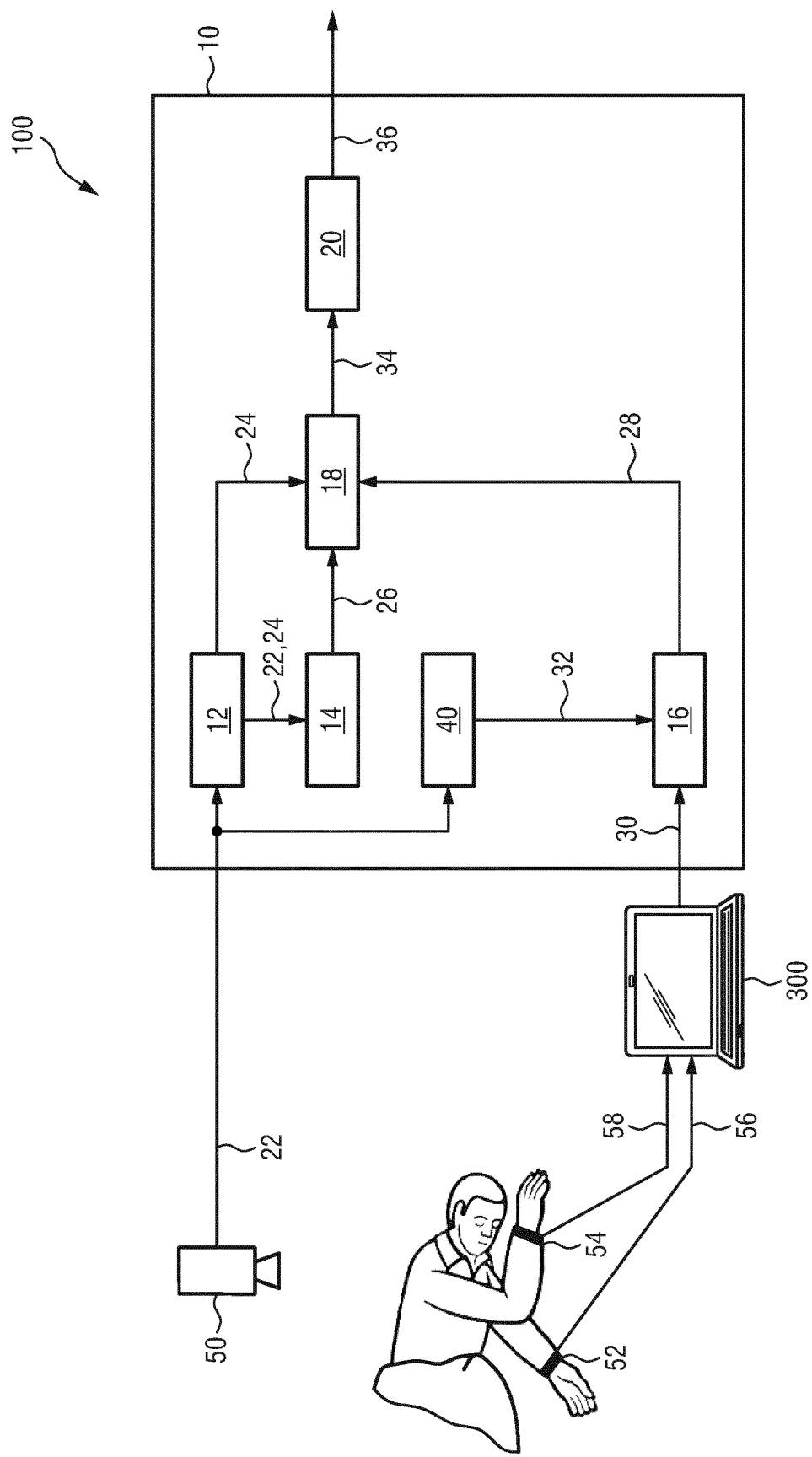
FIG. 5 shows a schematic diagram of a second embodiment of a system for providing a skeleton model of a patient according to the present invention.

FIG. 5 shows a schematic diagram of a second embodiment of a system 100 for providing a skeleton model 36 of a patient according to the present invention. The system 100 comprises a device 10, a left PPG sensor 52 attached to a left finger of the patient, a right PPG sensor 54 attached to a right finger of the patient, a camera 50 and a device 300 for localizing a sensor on a patient's body.

The left and right PPG sensors 52 and 54 provide left and right PPG signals 56 and 58, respectively. From each of the PPG signals 56 and 58, the device 300 (also referred to as patient monitor in the following) calculates the pulse arrival time. In general, a pulse arrival time from the left part of a body is shorter than the pulse arrival time from a right part of a body due to the location of the heart inside the body. A subsequent comparison of both pulse arrival times then allows the device 300 to localize the sensors 52 and 54 where the PPG signals originate from. A further comparison with reference values stored in the device 300 may refine the results and hence may refine the body location data 30. However, in case the signals 56 and 58 are too low, the patient monitor 300 is able to provide the body location data 30 due to various other means. For example, the side of the body to which the probe is connected may be manually entered by a nurse/clinical in the patient monitor 300. Alternatively, there may be used established clinical practices for a given care setting/hospital to which side of the body (left or right hand) a particular probe/sensor for monitoring is connected. The body location data 30 found by the device 300 is then provided to the sensor location unit 16 of the device 10 for further processing. At the same time, image location data 32 are generated. In order to do so, the images from the camera 50 are used to identify and locate the pulse oximetry cables connecting the sensors 52 and 54 to the patient monitor 300. This can be done by looking for the object features of the cable.

Once the sensor location unit 16 has received information from the patient monitor 300 and the sensor recognition unit 40 concerning the locations of the PPG sensors, the locations of the sensor are linked with the locations of the identified joints as being joints from the left or the right side of the body.

Figure 6:
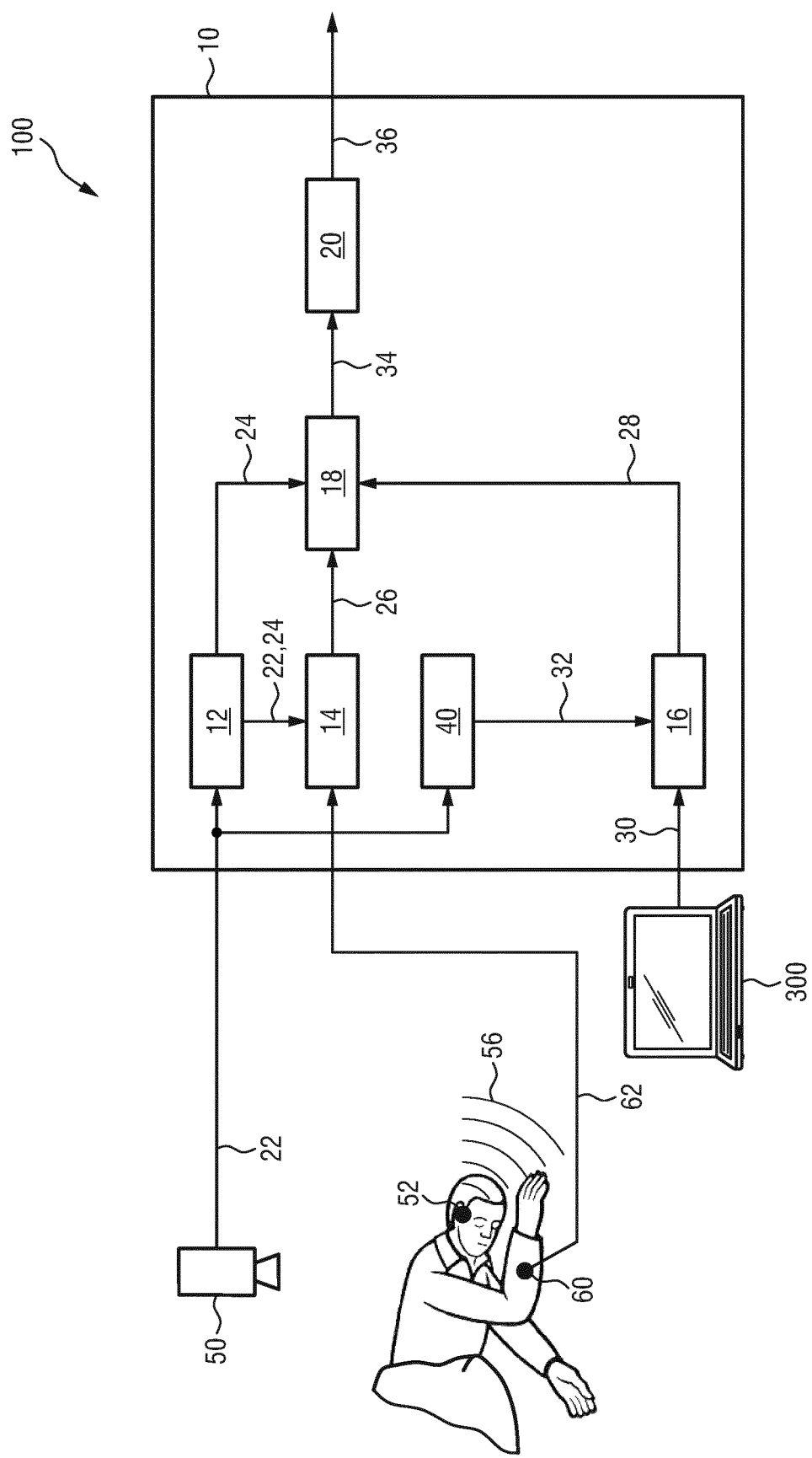
FIG. 6 shows a schematic diagram of a third embodiment of a system for providing a skeleton model of a patient according to the present invention.

FIG. 6 shows a schematic diagram of a third embodiment of a system 100 for providing a skeleton model 36 of a patient according to the present invention. The system 100 comprises a device 10, a PPG sensor 52 attached to the right temple of the patient, an ECG sensor attached to the patient's right arm, a camera 50 and a device 300 for localizing a sensor on a patient's body.

The PPG sensors 52 provides a PPG signal 56, from which the device 300 calculates the pulse arrival time. In this embodiment the PPG signal 56 is transmitted wirelessly. The device 300 compares the calculated pulse arrival time with reference values stored in a storage of the device 300 and uses said comparison to localize the sensor 52 on the patient's body. The body location data 30 found by the device 300 is then provided to the sensor location unit 16 of the device 10 for further processing. At the same time, image location data 32 are generated. In order to do so, the images from the camera 50 are used to identify and locate the PPG sensor 52 by its shape and externally applied pattern. Once the sensor location unit 16 has received information from the patient monitor 300 and the sensor recognition unit 40 concerning the location of the PPG sensor, the location of the sensor is linked to the location of a joint identified. In particular, said joint may be assigned to the patient's right body part.

The ECG sensor 60 attached to the patient's right arm provides ECG data 62 to the pose estimation unit 14, wherein the pose estimation unit 14 is configured to estimate the patient's pose (i.e. to generate pose estimation data 26) using the ECG data 62. Since the orientation of the heart axis depends on the body's position and orientation in the earth's gravitational field different body postures result in different ECG signals. In particular, by comparing the ECG data 62 with ECG patterns stored in the pose estimation unit 14, wherein said patterns are stored with corresponding poses, the pose estimation unit 14 may extract information about the patient's posture in his/her bed.

Figure 7:
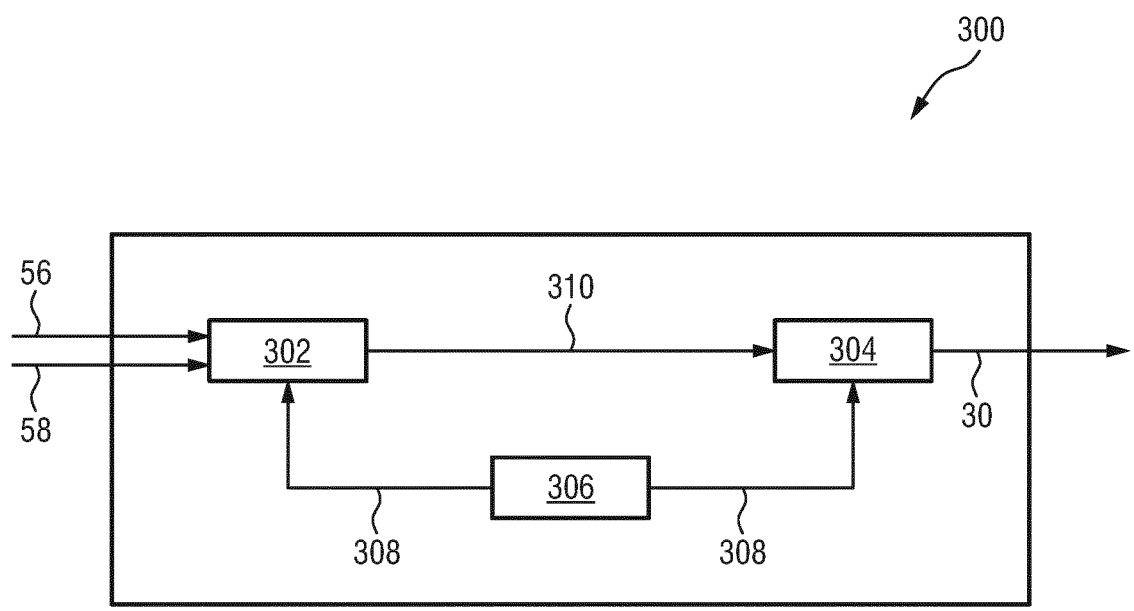
FIG. 7 shows a schematic diagram of an embodiment of a device for localizing a sensor on a patient's body according to the present invention.

FIG. 7 shows a schematic diagram of an embodiment of a device 300 for localizing a sensor on a patient's body. The device 300 comprises a comparison unit 302, an analysis unit 304 and a user interface 306. In this embodiment, the comparison unit 302 obtains a PPG signal 56 originating from the left part of the patient's body and a PPG signal 58 originating from a right part of the patient's body. In the comparison unit 302 both signals 56 and 58 are then compared to each other with respect to PPG signal properties (that possibly first have to be derived) comprising pulse strength and/or pulse arrival time. Furthermore, the signals 56 and 58 may be compared to reference values comprised in user information 308 provided by the user interface 306. Results of the comparison 310 are then provided to the analysis unit 304. Using the result of the comparison 310, the analysis unit 304 may assign to each of the PPG signals 56 and 58 a location on the patient's body where the signals originate from. In particular, the analysis unit 304 may assign whether the left and right PPG signals 56 and 58 come from either a left or a right body part. A more precise assignment may be achieved with the user information 308 provided by the user interface 306. For example, the user interface 306 may provide information that the PPG sensors are sensors used on the patient's fingers. Collecting all this information, the analysis unit 304 is able to generate sensor information data 28.

FIGS. 8A and 8B show PPG signals simultaneously obtained from a patient's left and right finger. The signals shown have been obtained with a sampling frequency of 2000 Hz. The signals are shown in an arbitrary unit but the signals from the left and right fingers are comparable in this unit. Only a time interval of the signals from the left and the rights sides are shown, with the x-axis depicting the sample number for the displayed time interval.

FIG. 8C shows the same PPG signals 81 and 82 from the left and right finger, respectively, along with a simultaneously measured ECG signal 83. The signals are plotted in an arbitrary unit along the y-axis and only the timing information of the signal features like the location of peak in the ECG signal and the PPG signals are intended to be conveyed with this figure by plotting all three signals together. All signals shown were synchronously recorded at a sampling frequency of 2000 Hz. Only a time interval of the whole recording is shown for clarity, with the x-axis in the figure representing the corresponding sample number. The peak of PPG has been used as it can be robustly detected to compute Pulse Arrival Time (PAT). Other PPG morphological fiducial points like the location of steepest upstroke can also be used for this purpose. The value of the maxima of the PPG signal may fluctuate due to the way the corresponding sensor has been attached to the body (e.g. how tight or loose).

Figure 9A:
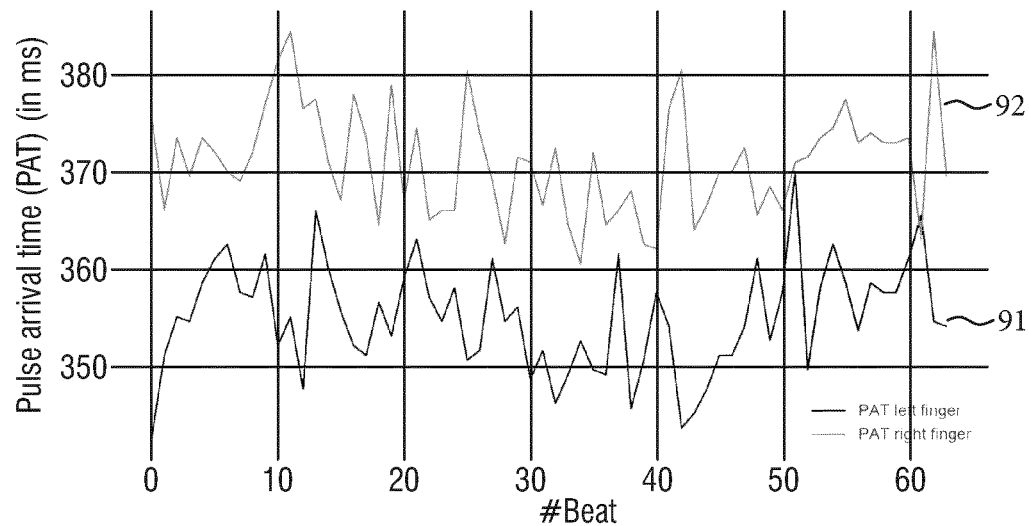
FIG. 9A shows the pulse arrival times as calculated from the left and right finger PPG signals, respectively.

FIG. 9A shows the pulse arrival times 91 and 92 as calculated from the left and right finger PPG signals, respectively. Pulse Arrival Time (PAT) is computed as the time difference between the maximum of the PPG signal and the maximum of the (corresponding) ECG signal. PAT can be computed for each beat in the cardiac cycle which is shown in the FIG. 9A with the computed PAT in milliseconds plotted in the y-axis. The corresponding beat number is shown in the x-axis to depict how PAT changes from beat-to-beat. It can be seen from FIG. 9A that the pulse arrival time 91 corresponding to a measurement at the patient's left finger is generally shorter than the pulse arrival time 92 corresponding to a measurement at the patient's right finger. The difference between both pulse arrival times ranges from 0 ms (−2 ms) to about 35 ms.

Figure 9B:
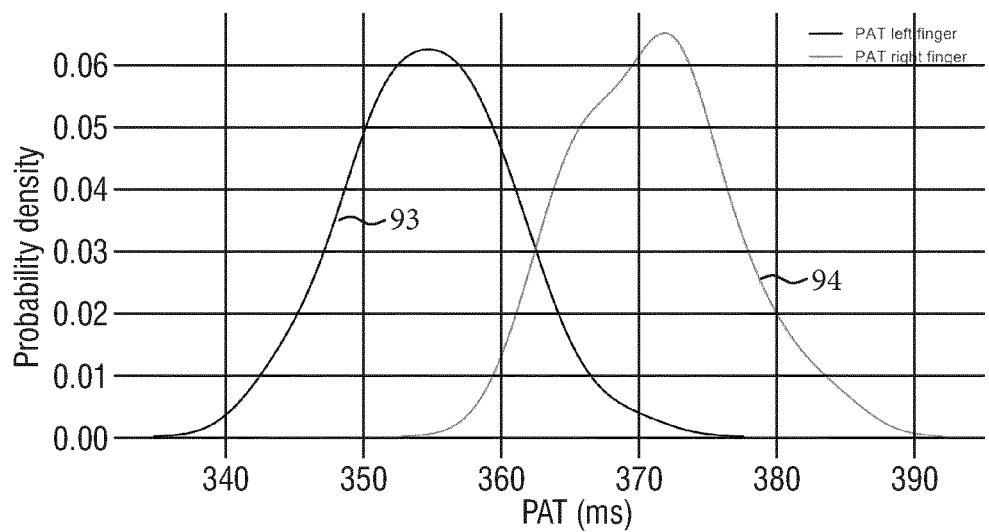
FIG. 9B shows the distribution of pulse arrival time values for the PPG signals from the left and right finger.

FIG. 9B shows the distribution 93 and 94 of pulse arrival time values for the PPG signals from the left and right finger, respectively. This distribution has been calculated using a kernel density estimation procedure on the PAT values plotted in FIG. 9A. According to FIG. 9B, the pulse arrival time for the right finger PPG signal is generally higher than the pulse arrival time for the left finger PPG signal. In most cases, the difference between PAT as measured at the left and right finger, respectively, is about 17 ms. This difference is due to the location of the heart in the human body. As the heart is usually located on the left-hand side of a human, the way the blood has to flow from the heart to a left finger is shorter than the way from the heart to a right finger. Accordingly, a pulse arrives earlier in a left finger than in a right finger.

Figure 10:
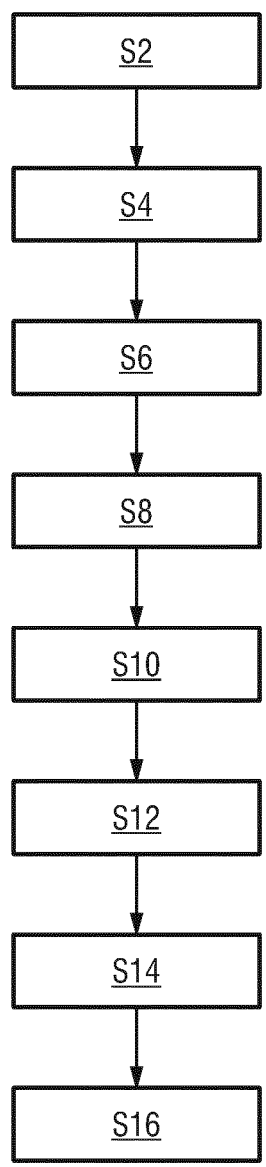
FIG. 10 shows a flow chart of a first embodiment of a method for providing a skeleton model of a patient according to the present invention.

FIG. 10 shows a flow chart of a first embodiment of a method for providing a skeleton model of a patient according to the present invention.

In a first step S2 a depth image of the patient and corresponding image data 22 is obtained from a computer, for example. In the next step S4 it is searched for patient sensors in the image. Sensor recognition may be facilitated by specific markers attached to the sensors. In this step, image location data 32 are generated. In step S6 joint location data 24 are generated by localizing one or more joints of the patient in the image represented by image data 22. While image location data 32 are generated in this first embodiment prior to joint location data 24, other embodiments with reversed order are conceivable as well. Using the joint location data 24 and/or the image data 22 itself there is estimated a posture of the patient in this bed in step S8. Accordingly, pose estimation data 26 are generated in this step. In step S10 body location data 30, comprising information about a location of a sensor on the patient's body, are obtained. By combining said data with the image location data 32 sensor location data 28 are generated in step S12. Subsequently, in step S14 information from the joint location data 24, the pose estimation data 26 and the sensor location data 28 are fused together to get a correct assignment between the joint locations in the image and body parts of the patient. Given the assignment of joints to the patient's body locations there is generated a skeleton model 36 in step S16.

Figure 11:
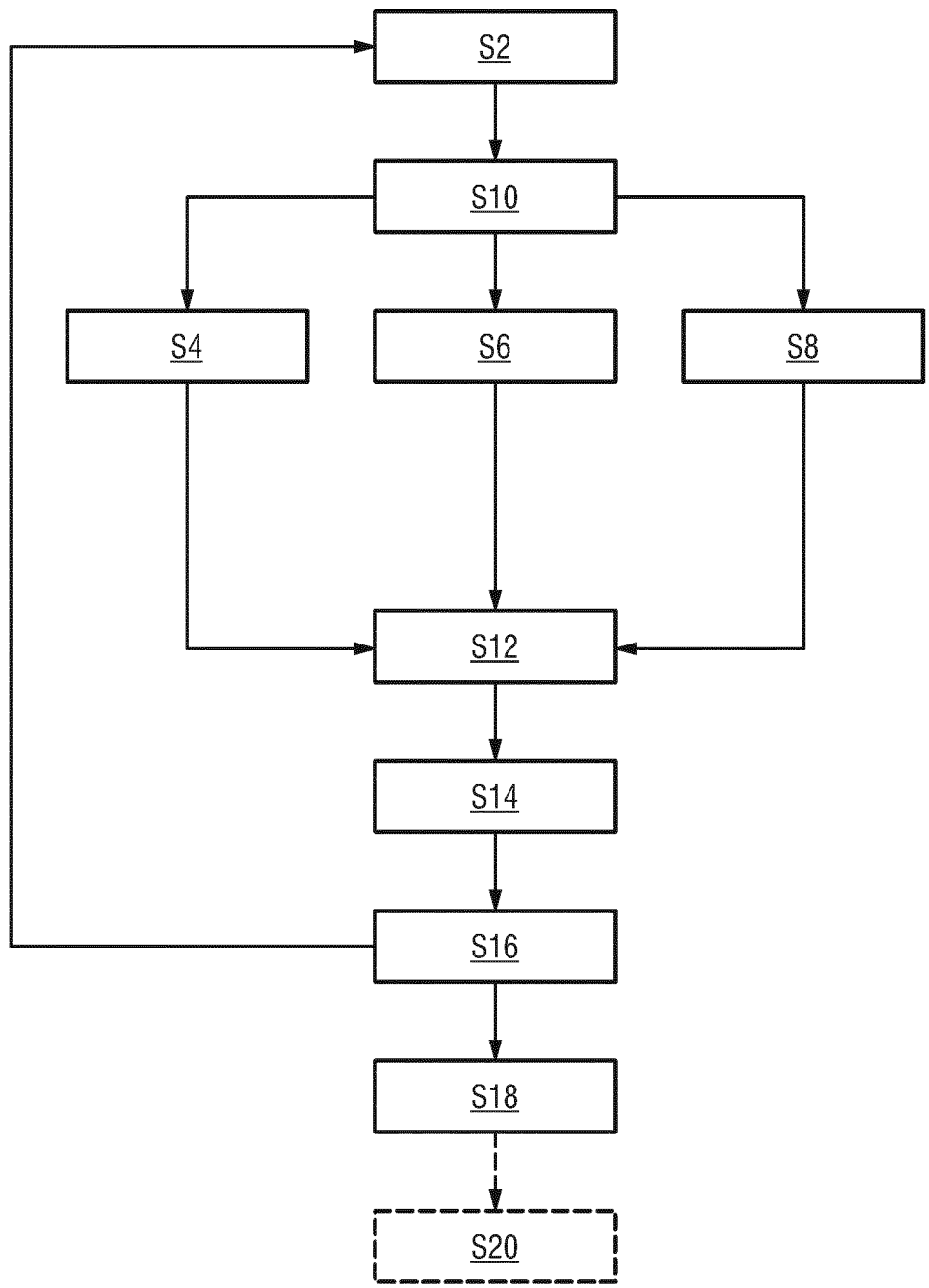
FIG. 11 shows a flow chart of a second embodiment of a method for providing a skeleton model of a patient according to the present invention.

FIG. 11 shows a flow chart of a second embodiment of a method for providing a skeleton model of a patient according to the present invention.

Contrary to the first embodiment of the method, in the second embodiment of the method body location data 30 are obtained directly after obtaining image data 22 of a patient. Then, using the image data 22, there are generated simultaneously joint location data 24, pose estimation data 26 and image location data 32 in steps S4, S6 and S8. In step S12 the image location data 32 and the body location data 30 are linked to each other to generate sensor location data 28. In step S14 the sensor location data 28, the joint location data 24 and the pose estimation data 26 are fused together to perform joint disambiguation, i.e. to get a correct assignment between the joint locations in the image. Given the assignment of joints to the patient's body locations there is generated a skeleton model 36 in step S16. Subsequently, the process for generating a skeleton model from another image is started (S2). Once at least two skeleton models 36 corresponding to different images 22 are generated, the different skeleton models are compared to each other in S18 for tracking patient movements. Furthermore, the comparison is used in this step to refine the methods used to obtain the skeleton model and to refine the skeleton model 36 itself. In an optional step S20 the comparison results may further be used to refine the identification and localization of joints in the joint identification unit 12.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for providing a skeleton model of a patient, the device comprising:
  a joint identifier configured to obtain an image and corresponding image data of the patient including depth information and to generate joint location data by localizing one or more joints of the patient in said image;
  a pose estimator configured to generate pose estimation data by estimating a pose of the patient using the joint location data and/or the image data,
  a sensor locator configured to obtain body location data; including information about a location of a sensor on a body of the patient, and image location data including information about the location of the sensor in the image, and to generate sensor location data, assigning a sensor location in the image to a body location of the patient, based on the body location data and the image location data;

an assignor configured to perform an assignment of the one or more joints to one or more body locations of the patient by using the joint location data, the pose estimation data and the sensor location data; and a skeleton model generator configured to generate a skeleton model of the patient based on the assignment of the one or more joints to one or more body locations of the patient.

2. The device according to claim 1, further comprising a sensor informer configured to obtain a sensor signal corresponding to a vital sign of the patient and to generate the body location data and/or the pose estimation data based on said sensor signal.

3. The device according to claim 2, wherein the sensor signal corresponding to a vital sign includes any one of electrocardiogramata, photoplethysmography data, blood pressure data, body temperature data, blood oxygen saturation data, pulse rate data, pulse strength data and pulse arrival time data.

4. The device according to claim 1, further comprising a sensor recognizer configured to generate the image location data by localizing the sensor in the image.

5. The device according to claim 1, wherein the pose estimator is configured to generate the pose estimation data further using the sensor location data.

6. The device according to claim 1, wherein the pose estimator is configured to distinguish between:
a supine pose, wherein the patient is lying in a supine pose;
a prone pose, wherein the patient is lying prone; and
a side pose, wherein the patient is lying on a side of his or her body.

7. The device according to claim 1, wherein the pose estimator is configured to estimate the pose of the patient by identifying a distribution of the one or more joints in the image.

8. The device according to claim 1,
wherein the joint identifier is configured to localize one or more extreme points in the image; and
wherein the pose estimator is configured to estimate the pose of the patient by identifying a distribution of said extreme points in the image.

9. The device according to claim 1, wherein the joint identifier localizes the one or more joints using a machine learning method, particularly a deep learning algorithm, more particularly a convolutional neural network.

10. The device according to claim 1, further comprising a tracker configured to track movements of the patient based on two or more subsequent depth images and the corresponding two or more skeleton models.

11. The device according to claim 10,
wherein the tracker is configured to perform a comparison between the two or more skeleton models;
wherein the joint locator is configured to adapt the joint location data based on said comparison, and/or
wherein the skeleton model generator is configured to adapt the skeleton models based on said comparison.

12. A system for providing a skeleton model of a patient, the system comprising:
a device for providing a skeleton model of a patient as claimed in claim 1; and
one or more sensors configured to generate one or more sensor signals by detecting one or more vital signs of the patient and/or a depth camera configured to acquire an image of the patient and to generate corresponding image data comprising depth information.

13. A method for providing a skeleton model of a patient, the method comprising the steps of:
obtaining an image and corresponding image data of the patient including depth information and generating joint location data by localizing one or more joints of the patient in said image ;;
generating pose estimation data by estimating a pose of the patient using the joint location data and/or the image data;
obtaining body location data including information about a location of a sensor on a body of the patient, and image location data including information about the location of the sensor in the image, and generating sensor location data assigning a sensor location in the image to a body location of the patient based on the body location data and the image location data;
performing an assignment of the one or more joints to one or more body locations of the patient by using the joint location data, the pose estimation data and the sensor location data; and
generating a skeleton model of the patient based on the assignment of the one or more joints to one or more body locations of the patient.

14. A non-transitory computer-readable medium that stores therein a computer program for providing a skeleton model of a patient which, when executed on a computer, causes the computer to carry out the steps of the method as claimed in claim 13.

* * * * *